(12) United States Patent
Meglan et al.

(10) Patent No.: US 12,357,406 B2
(45) Date of Patent: Jul. 15, 2025

(54) ROBOTIC SURGICAL COLLISION DETECTION SYSTEMS

(71) Applicant: Covidien LP, Mansfield, MA (US)

(72) Inventors: Dwight Meglan, Westwood, MA (US);
Meir Rosenberg, Newton, MA (US);
William J. Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 862 days.

(21) Appl. No.: 17/432,644

(22) PCT Filed: Mar. 16, 2020

(86) PCT No.: PCT/US2020/022894
§ 371 (c)(1),
(2) Date: Aug. 20, 2021

(87) PCT Pub. No.: WO2020/190832
PCT Pub. Date: Sep. 24, 2020

(65) Prior Publication Data
US 2022/0160445 A1 May 26, 2022

Related U.S. Application Data (60) Provisional application No. 62/820,908, filed on Mar. 20, 2019.

(51) Int. Cl.
*A61B 34/00* (2016.01)
*A61B 34/20* (2016.01)
(Continued)

(52) U.S. Cl.
CPC .............. *A61B 34/37* (2016.02); *A61B 34/25* (2016.02); *A61B 50/13* (2016.02); *B25J 9/1676* (2013.01);
(Continued)

(58) Field of Classification Search
CPC ......... A61B 34/37; A61B 34/25; A61B 50/13; A61B 2034/2057; A61B 2034/2059;
(Continued)

(56) References Cited

U.S. PATENT DOCUMENTS 8,828,023 B2 9/2014 Neff et al.
9,452,531 B2 9/2016 Kikkeri et al.
(Continued)

FOREIGN PATENT DOCUMENTS

KR 10-2018-0109855 A 10/2018
WO 2014093367 A1 6/2014
(Continued)

OTHER PUBLICATIONS

Safe_human-robot_interaction_based_on_dynamic_sphere-swept_line_2011.pdf (Year: 2011).*
(Continued)

*Primary Examiner* — Kyle T Johnson
(74) *Attorney, Agent, or Firm* — Carter, DeLuca & Farrell LLP (57) ABSTRACT

Systems and methods for surgical robotic collision detection in accordance with aspects of the present disclosure are disclosed. In various embodiments, a system for surgical robotic collision detection includes a robotic cart having a robotic arm, an imaging device supported by the robotic cart or the robotic arm, the imaging device captures images within a field of vision of the imaging device, and a controller in operable communication with the robotic arm and the imaging device. The controller includes a processor and a memory storing instructions which, when executed by the processor, causes the controller to: receive the images from the imaging device, generate a grid including a first
(Continued)

plurality of spatial points from the images, and detect a potential collision within the field of vision based on the generated grid.

22 Claims, 7 Drawing Sheets

(51) Int. Cl.
  *A61B 34/30* (2016.01)
  *A61B 34/37* (2016.01)
  *A61B 50/13* (2016.01)
  *B25J 9/16* (2006.01)

(52) U.S. Cl.
  CPC .......... *A61B 2034/2057* (2016.02); *A61B 2034/2059* (2016.02); *A61B 2034/2065* (2016.02); *A61B 2034/302* (2016.02); *A61B 2034/742* (2016.02); *A61B 2034/743* (2016.02); *A61B 2034/744* (2016.02)

(58) Field of Classification Search
  CPC ...... A61B 2034/2065; A61B 2034/302; A61B 2034/742; A61B 2034/743; A61B 2034/744; B25J 9/1676
  See application file for complete search history.

(56) References Cited

U.S. PATENT DOCUMENTS

| | | | | |
|---|---|---|---|---|
| 2003/0109780 | A1* | 6/2003 | Coste-Maniere | G06T 7/0012 600/407 |
| 2010/0080417 | A1* | 4/2010 | Qureshi | G16H 50/20 700/59 |
| 2012/0182392 | A1 | 7/2012 | Kearns et al. | |
| 2017/0177937 | A1 | 6/2017 | Harmsen et al. | |
| 2017/0333137 | A1* | 11/2017 | Roessler | A61B 34/10 |
| 2018/0222050 | A1* | 8/2018 | Vu | B25J 9/1694 |
| 2019/0011921 | A1 | 1/2019 | Wang et al. | |
| 2019/0066314 | A1 | 2/2019 | Abhari et al. | |
| 2019/0160677 | A1* | 5/2019 | Strandberg | B25J 9/163 |
| 2019/0193267 | A1* | 6/2019 | Peng | B25J 9/1664 |
| 2021/0053227 | A1* | 2/2021 | Wartenberg | B25J 19/06 |
| 2021/0086359 | A1* | 3/2021 | Eberst | B25J 9/1671 |
| 2022/0080594 | A1* | 3/2022 | Sorin | G05D 1/0214 |
| 2022/0126451 | A1* | 4/2022 | Hopkinson | B25J 9/1676 |
| 2022/0160445 | A1* | 5/2022 | Meglan | B25J 9/1676 |
| 2022/0193911 | A1* | 6/2022 | Floyd-Jones | B25J 9/1666 |
| 2023/0234230 | A1* | 7/2023 | Aas | B25J 11/005 700/255 |

FOREIGN PATENT DOCUMENTS

| | | |
|---|---|---|
| WO | 2017210098 A1 | 12/2017 |
| WO | 2018086133 A1 | 5/2018 |
| WO | 2019050822 A1 | 3/2019 |
| WO | 2019136039 A1 | 7/2019 |

OTHER PUBLICATIONS

Extended European Search Report dated Oct. 31, 2022 corresponding to counterpart Patent Application EP 20773971 .5.
Office Action dated Jul. 29, 2023 for Chinese Patent Application No. 202080022383.6 (22 pages).
International Search Report mailed Jul. 6, 2020 and Written Opinion completed Jul. 6, 2020 corresponding to counterpart Int'l Patent Application PCT/US20/22894.

* cited by examiner

ROBOTIC SURGICAL COLLISION DETECTION SYSTEMS

CROSS-REFERENCE TO RELATED APPLICATIONS

The present application is a U.S. National Stage Application filed under 35 U.S.C. § 371(a) claiming the benefit of and priority to International Patent Application No. PCT/US2020/022894, filed Mar. 16, 2020, which claims the benefit of and priority to U.S. Provisional Patent Application Ser. No. 62/820,908, filed Mar. 20, 2019, the entire disclosures of each of which being incorporated by reference herein.

BACKGROUND

Robotic surgical systems are commonly used to perform minimally invasive medical procedures. These surgical systems may include a surgeon console configured to control a movable support structure (e.g., a movable cart) supporting a robotic arm with at least one end effector (e.g. forceps, a grasping tool, and/or camera) mounted thereto. The robotic arm may provide mechanical and/or electrical power to the end effector during surgical procedures. In addition, the robotic arm may also enable electrical communication between the end effector and computing devices to control operation of the end effector during surgical procedures. Each robotic arm may include an instrument drive unit operatively connected to the end effector, the instrument drive unit containing at least one drive mechanism.

The surgeon console generally includes one or more handle assemblies for actuating functions to control an associated end effector during surgical procedures. These handle assemblies implement actuation either via direct mechanical translation of force exerted by a user or by translating user actuation of the handle assemblies into control signals which, in turn, are transmitted to the robotic arm to actuate the drive mechanisms of the instrument drive unit and/or the end effector. Depending on the control signals generated in response to user manipulation of the handle assemblies, the various controlled components may make minor positional adjustments to move the robotic arms and/or the end effectors a few millimeters to more significant adjustments of decimeters or meters within the surgical field. These adjustments may lead to collisions between the various controlled components and/or other objects (e.g., a surgical table or support staff) in a surgical environment.

Accordingly, there is a need for systems and methods of identifying and mitigating potential collisions between controlled components and objects (e.g., various controlled components and/or other objects) within a surgical environment as the various controlled components move within the surgical environment.

SUMMARY

In accordance with an aspect of the present disclosure, a surgical robotic collision detection system is described. The surgical robotic collision detection system includes a robotic cart having a robotic arm, an imaging device, and a controller. The imaging device is supported by the robotic cart or the robotic arm and configured to capture images within a field of vision of the imaging device. The controller is in operable communication with the robotic arm and the imaging device. The controller includes a processor and a memory storing instructions thereon which, when executed by the processor, causes the controller to receive the image from the imaging device, generate a grid including a first plurality of spatial points from the images, and detect a potential collision within the field of vision based on the generated grid.

The imaging device may be a stereoscopic imaging device, an optical imaging device, a ranging laser device, an infrared (IR) imaging device, an imaging device for depth (e.g., an RGB-D imaging device). The imaging device may include a sensor configured to capture the first image at a first time point.

In accordance with aspects of the present disclosure, a surgical robotic collision detection system includes a robotic cart having a robotic arm, and an imaging device supported by the robotic cart or the robotic arm. The imaging device captures images within a field of vision of the imaging device. A controller is in operable communication with the robotic arm and the imaging device. The controller has a processor and a memory storing instructions which, when executed by the processor, causes the controller to: receive the images from the imaging device; generate a grid including a first plurality of spatial points from the images; and detect a potential collision within the field of vision based on the generated grid.

In another aspect of the present disclosure, the imaging device includes a sensor configured to capture a first image at a first time point, the first image including an object in positional relation to the sensor.

In an aspect of the present disclosure, the memory stores instructions which, when executed by the processor, causes the controller to receive the first image and generate a first depth map based on the first image.

In yet another aspect of the present disclosure, the controller generates a first point cloud based on the first depth map, the first point cloud including the first plurality of spatial points contained within the grid.

In a further aspect of the present disclosure, the controller segments the first plurality of spatial points to identify a first spatial point subset of the first point cloud, each spatial point in the first spatial point subset corresponds to a surface of the object.

In an aspect of the present disclosure, the memory includes instructions that, when executed by the processor, causes the controller to: compare the first spatial point subset to a pre-identified configuration of a structure of the object to identify the object within the field of vision of the imaging device.

In a further aspect of the present disclosure, the sensor of the imaging device captures a second image at a second time point, and the memory further includes instructions that, when executed by the processor, causes the controller to: receive the second image; and generate a second depth map.

In yet another aspect of the present disclosure, the memory further includes instructions that, when executed by the at least one processor, causes the controller to: generate a second point cloud within the coordinate system including a second plurality of spatial points, and where the second point cloud is based on the second depth map.

In a further aspect of the present disclosure, the memory further includes instructions that, when executed by the at least one processor, causes the controller to: segment the second plurality of spatial points to identify a second spatial point subset of the second point cloud and compare the second spatial point subset to the pre-identified configuration of a structure of the one or more objects; match the first spatial point subset in the first point cloud with the second spatial point subset in the second point cloud to orient the first point cloud with the second point cloud; and identify motion of the one or more objects within the field of vision of the imaging device based on the orientation of the first point cloud relative to the second point cloud.

In yet a further aspect of the present disclosure, the memory further includes instructions that, when executed by the one or more processors, causes the controller to determine a spatial trajectory (e.g., positional trajectory and/or orientation direction) of the one or more objects based upon the identified motion of the one or more objects from the position of the one or more objects in the first point cloud to the position of the one or more objects in the second point cloud.

In yet another aspect of the present disclosure, the method further includes a display device in communication with the controller. The memory further includes instructions stored thereon which, when executed by the processor, causes the controller to: cause the display device to output an indication of a possible collision based on determining that a possible collision exists.

In a further aspect of the present disclosure, the indication includes three-dimensional images of a position diagram.

In yet a further aspect of the present disclosure, the three-dimensional images of the position diagram illustrate a rendering of the possible collision at a later point in time in a case where the object remains on the spatial trajectory.

In a further aspect of the present disclosure, the memory further includes instructions stored thereon which, when executed by the processor, causes the controller to: transmit a control signal to the robotic cart or the robotic arm to cause the robotic arm to reposition to avoid the possible collision.

In an aspect of the present disclosure, a method for detecting potential collisions between objects of a surgical robotic system including an imaging device, a robotic arm, and a controller, the controller in communication with the imaging device and the robotic arm. The method includes receiving image data captured by the imaging device, generating a depth map including a first plurality of spatial points based on the image data, and detecting a potential collision between objects captured in the image data.

In another aspect of the present disclosure, the method further includes generating a first point cloud based on the depth map, the first point cloud including the plurality of spatial points.

In a further aspect of the present disclosure, the method further includes segmenting the plurality of spatial points in the point cloud to identify a spatial point subset of the point cloud, each point in the spatial point subset corresponds to a surface portion of the one or more objects.

In yet another aspect of the present disclosure, the identifying of the spatial point subset includes matching the spatial point subset to a predetermined configuration of the one or more objects and, based on the matching, identifying the one or more objects.

In an aspect of the present disclosure, the method further includes: receiving second image data from the imaging device at a point in time later than when the image data was captured by the imaging device, generating a second depth map including a second plurality of spatial points based on the second image data, generating a second point cloud including a second plurality of spatial points based on the second depth map, segmenting the second plurality of spatial points to identify the spatial point subset within the second point cloud, and matching the spatial point subset in the first point cloud with the spatial point subset in the second point cloud.

In another aspect of the present disclosure, the method further includes determining a spatial trajectory of the object based on the positional difference of the spatial point subset matched in the first point cloud and the second point cloud, and displaying an indication of a possible collision when a possible collision exists.

In a further aspect of the present disclosure, the method further includes transmitting a control signal to cause the robotic arm to modify motion in a direction to avoid the possible collision.

In an aspect of the present disclosure, a non-transitory computer readable medium that stores computer-executable instructions that causes at least one processor to execute a collision detection process is presented. The collision detection process includes receiving one or more images from an imaging device, generating a depth map including spatial points, each spatial point corresponding to a surface portion of one or more objects within a field vision of the imaging device, generating a point cloud based on the generated depth map, segmenting the spatial points in the point cloud into spatial point subsets, the spatial point subsets associated with objects in a surgical environment, and detecting a possible collision between spatial point subsets based on a range of motion of each of the spatial point subsets within the surgical environment.

Although embodiments of the present disclosure are described in detail with reference to the accompanying drawings for the purpose of illustration and description, it is to be understood that the disclosed embodiments are not to be construed as limited thereby. It will be apparent to those of ordinary skill in the art that various modifications and/or combinations to the foregoing embodiments may be made without departing from the scope of the present disclosure.

DETAILED DESCRIPTION

Embodiments of the present disclosure are described in detail with reference to the drawings, in which like reference numerals may be used to designate identical or corresponding elements in each of the several views.

The term "distal" as used herein generally refers to the portion of the component being described that are further from a clinician and closer to the patient, and the term "proximal" generally refers to the portion of the component being described which is closer to the clinician and further from the patient.

The term "clinician" as used herein generally refers to a doctor, a nurse, a healthcare provider including support personnel, and other operators of the surgical system described herein.

The term "surgical environment" as used herein generally refers to the space in which a surgical robot is disposed and operates within. Such space may include, but is not limited to, an operating room, a surgical robot storage and maintenance facility, and other space in which the surgical robot is disposed for mechanical operation. The term "surgical space" generally refers to an area within the surgical environment disposed within the patient and may include, without limitation, an insufflated or otherwise established region within the body of a patient.

The term "objects" as used herein generally refers to the corresponding components of a robotic surgical system, as well as foreign objects (e.g., tables, walls, movable carts, clinicians, or any other elements) located within the surgical environment, particularly those capable of collision with components of the described robotic surgical system.

The term "collision" as used herein generally refers to contact between objects within a surgical space or a surgical environment. Such collisions of objects may include, without limitation, a robotic arm contacting another robotic arm within the surgical environment during a surgical procedure. Collisions may further include collisions between robotic arms of robotic surgical systems and individuals or non-robotic elements. As used herein, robotic arm is understood to include tele-operated arms and the like.

The term "reference frame" as used herein generally refers to a predetermined area within which a sensor may collect measurements such as, for example, a three-dimensional coordinate frame which exists in fixed relation to a sensor.

The terms "wireless" refers to electrical communication of data or power between two points not connected by an electrical conductor. It will be understood that, throughout this disclosure, the terms "communication," "coupled to," and "wired" may describe connections which, in embodiments, may be substituted with wireless connections.

The present disclosure relates generally to the detection of possible collisions between objects in a surgical environment or in a surgical space (e.g., within a body of a patient). More particularly, the present disclosure describes systems and methods that detect possible collisions based on identified spatial relationships between objects in a surgical environment or a surgical space. These collisions may be detected based on sensor data received by one or more imaging devices positioned about the surgical environment. The imaging devices may be configured to measure the depth (e.g., distance) of portions of the surfaces of objects, such as robotic arms, relative to the imaging devices. A controller receives the measured depth information, referred to as image data, and generates a three-dimensional representation or depth map of the image data.

Where multiple instances of image data are available and/or where multiple imaging devices are disposed about the surgical environment, the corresponding image data may be associated or matched and discrete depth maps may be generated. Each depth map may contain spatial points within a fixed 3D space or reference frame. Combining the discrete depth maps enables the generation of a three-dimensional depth-map referred to as a point cloud. It is contemplated that a single imager may be used to produce depth for each of its pixels. As used herein, a point cloud is an accumulation of multiple depth images which may be from the same imager as that imager moves about, or it may be from multiple imagers either simultaneously or over time. The point cloud includes a plurality of spatial points and may, upon generation, be displayed as a model to illustrate the position and orientation (or "pose") of each of the objects within, and relative to, the surgical environment or surgical space.

In the depth maps or point clouds, when available, one or more predetermined object maps (e.g., sets of points that defines the exterior of objects) associated with specific objects (e.g., a link in a robotic arm linkage) may be matched with subsets of spatial points within the depth map or point cloud to identify the position of the specific object within the surgical environment. These object maps may also be generated based on a kinematic map derived from position signals representing the position and/or pose of the objects relative to one another (e.g., an encoder signal representing the position of a first linkage relative to another linkage). Where matched, the depth map or point cloud is updated based on the matched object maps to include spatial points from the object maps not included in the depth map or point cloud (e.g., known spatial points which are omitted from the initial depth map or point cloud and their positions relative to the matched points of the objects).

Potential collisions between objects imaged within the surgical environment or surgical space may be detected by calculating trajectories of the objects within the surgical environment or surgical space. For example, depth maps generated from image data may be analyzed over a period of time and the position of objects may be monitored to determine potential trajectories of the objects. When these potential trajectories intersect, potential collisions may be identified as likely to occur. Based on the identification of these potential collisions, three-dimensional images of a potential collision between the objects may be displayed on a display so a clinician can take action to avoid the collision. The controller may also transmit modified control signals to adjust movement or positioning of the objected identified as potentially subject to a collision.

Figure 1:
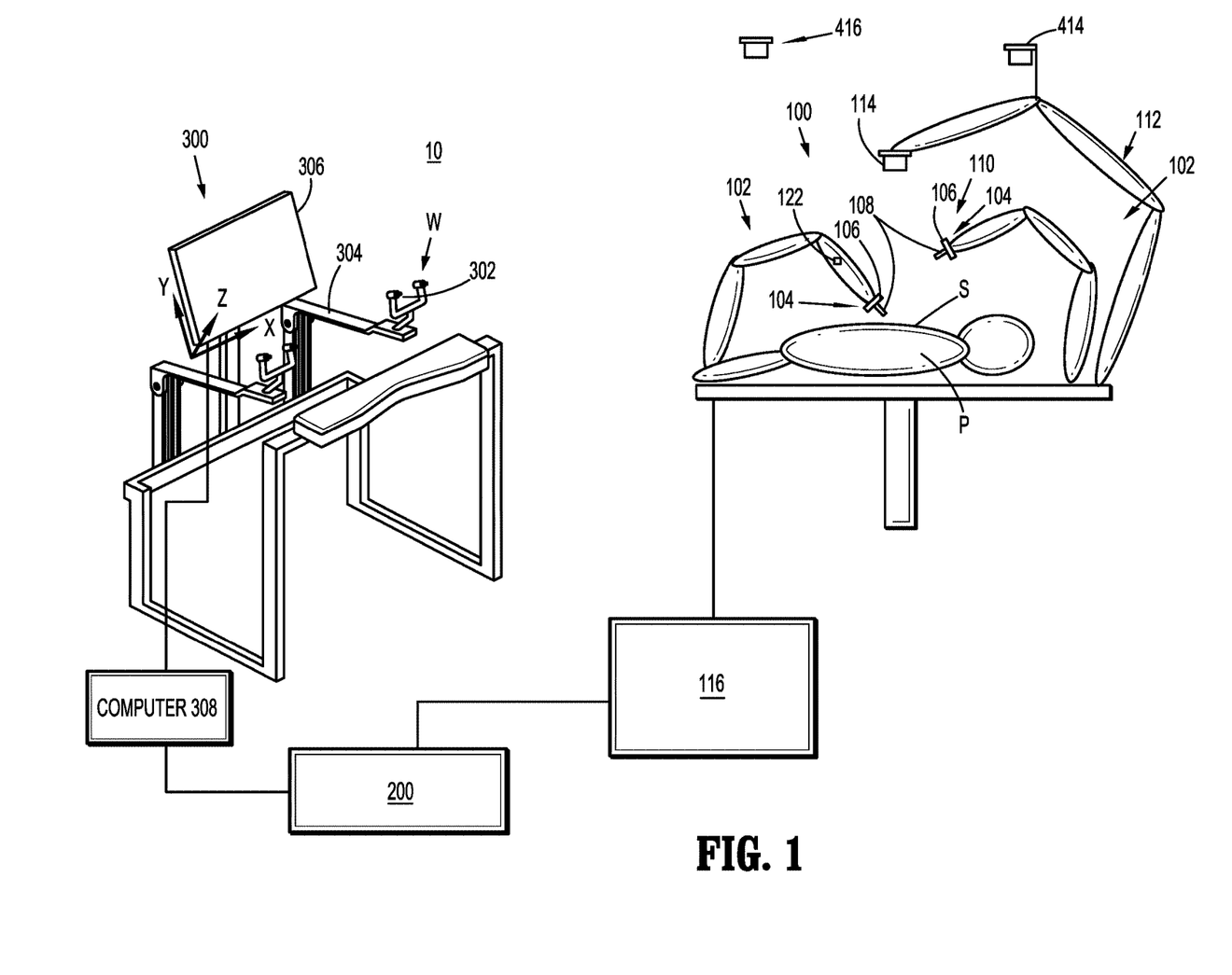
FIG. 1 is a schematic diagram of a robotic surgical system, according to an embodiment of the present disclosure.
Figure 2:
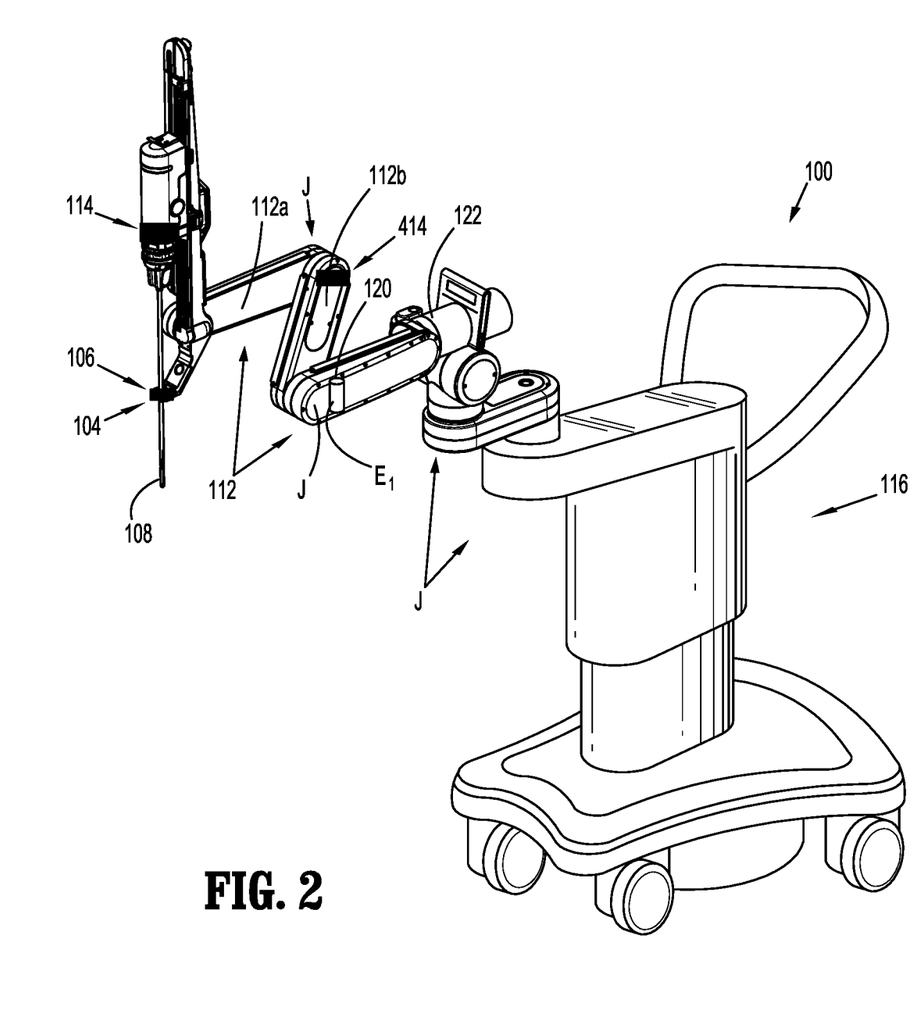
FIG. 2 is a perspective view of a robotic cart or tower of the robotic surgical system of FIG. 1.
Figure 3:
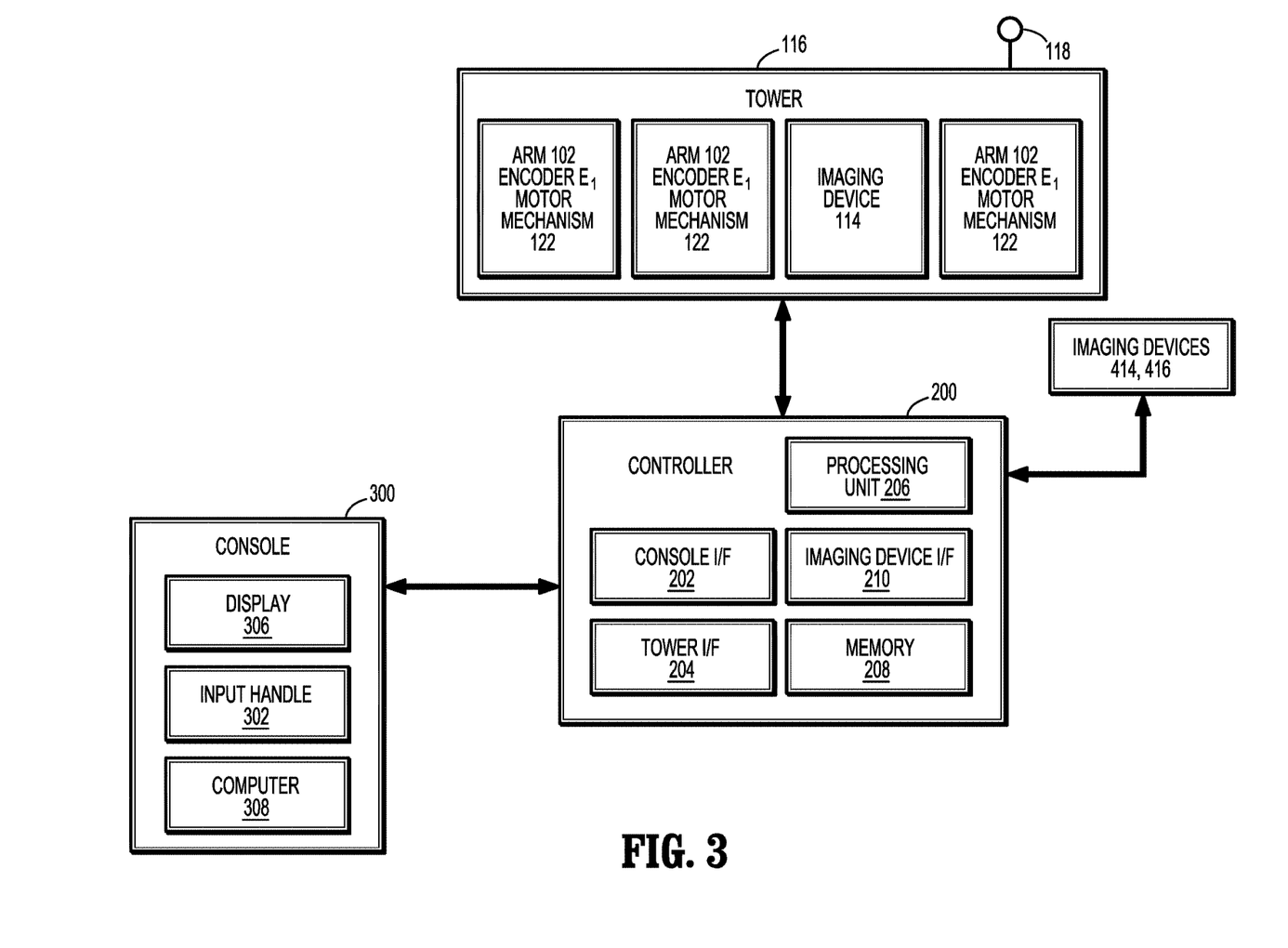
FIG. 3 is a schematic diagram of the system architecture for controlling the robotic surgical system of FIG. 1.

Referring now to FIGS. 1-3, a robotic surgical system provided in accordance with an embodiment of the present disclosure is illustrated and designated generally 10. The robotic surgical system 10 includes a surgical robot 100, a controller 200, and a user interface or console 300 including a display 306. The surgical robot 100 includes a robotic cart or tower 116. A linkage 112 is supported by the tower, the linkage 112 including a plurality of links 112a, 112b. The links 112a, 112b are rotatable relative to corresponding links 112a, 112b, each linkage 112 movably supporting an end effector or tool 108 (e.g., a camera) on an end portion 104 of the linkage 112 such that the end effector or tool 108 is configured to act on, or image, tissue of a patient "P" in a surgical space "S". The links 112a, 112b may pivot relative to one another to position the end portion 104 of the surgical robot 100 as desired during surgical procedures. The end portions 104 of robotic arms 102 may include an imaging device 106 configured for insertion into a surgical space "S" during surgical procedures. Additionally or alternatively, an imaging device 114 may be positioned along a distal portion of a robotic arm 102 and configured to capture image data including the entry point of the tools 108 disposed within the surgical space "S". As used herein, the imaging device 106 may include imaging sensors, cameras, laparoscopes, endoscopes and the like.

The tower 116 includes a communications interface 118 that receives communications and/or data from a tower interface 204. The communications interface 118 transmits signals to manipulate the motor 122 and move the linkages 112 associated with the tower 116. The motor 122 may be located in the robotic arm 102 and/or within discrete links 112a, 112b. In various embodiments, the motor 122 mechanically manipulates the robotic arm 102, the links 112a, 112b, and/or the tool 108 (FIG. 1) in response to receiving power. Mechanical manipulation of the robotic arm 102, linkages 112, and/or the tool 108 may include application of force from the motor 122 to move the robotic arm 102 and/or the tool 108 coupled to the robotic arm 102, in response to instructions from the processor 206. For example, the motor 122 may be operably coupled to a joint "J" via cables (not shown) to manipulate the robotic arm 102.

The tower 116 may be fixed within the surgical environment as shown in FIG. 1, or may be a movable cart repositionable within the surgical environment as shown in FIG. 2. The links 112a, 112b include motors 122 associated with respective joints "J" connecting the links 112a, 112b of the linkages 112. The motors 122 are configured to receive electrical power and/or control signals from the controller 200 and, in response, manipulate the position of the linkage 112 and/or the tool 108 within the surgical environment and/or the surgical space "S". Specifically, in response to the received control signals, the surgical robot 100 may activate a motor 122 to apply force about or to respective joints "J" to adjust the position of the various components of the surgical robot 100. The respective joints "J" of the linkages 112 may include encoders $E_1$. The encoders $E_1$ are disposed about the respective joints "J" of the linkage 112 and configured to generate encoder signals representative of the position and/or velocity of the linkages 112 about the respective joint "J" and, by extension, corresponding links 112a, 112b rotatably coupled about the joint "J".

Figure 4:
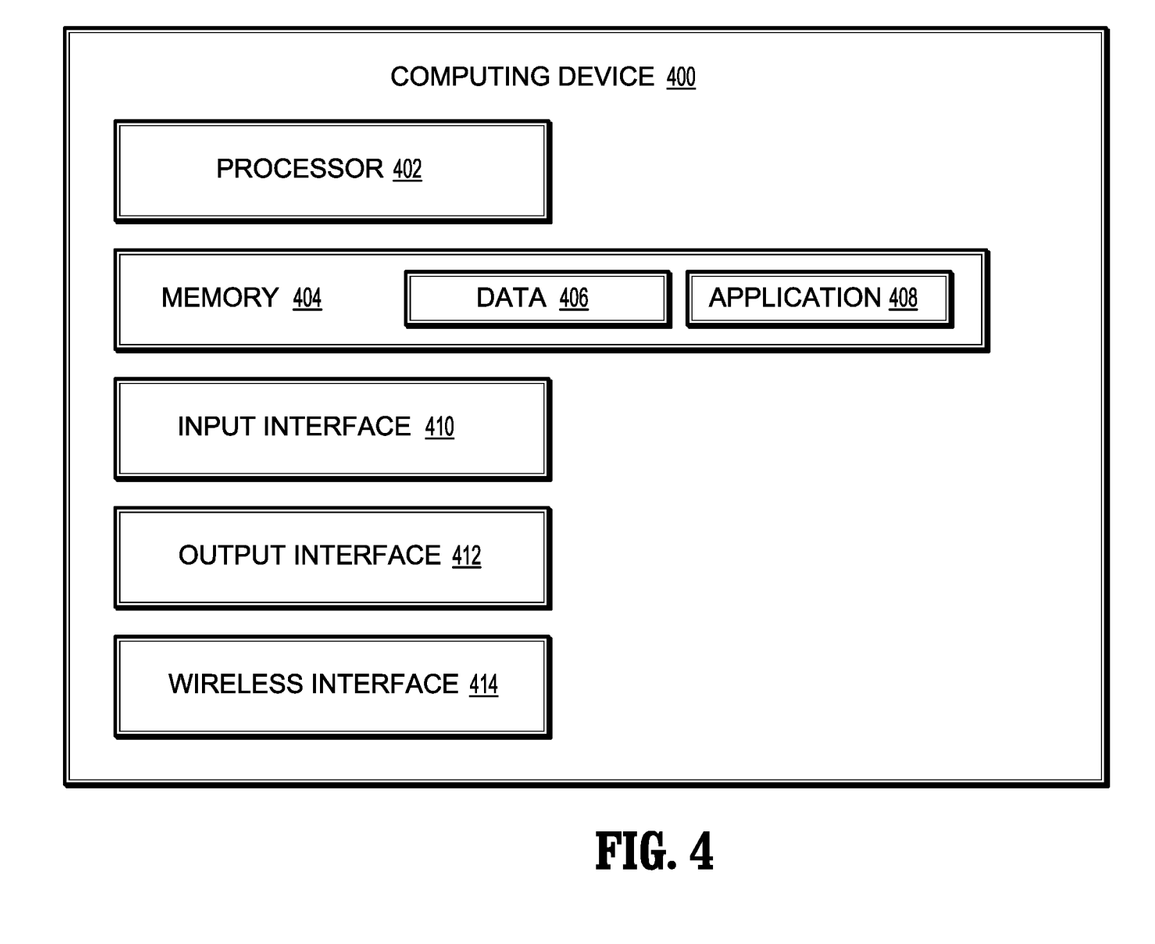
FIG. 4 is a schematic diagram of a computing device that may be employed according to various embodiments of the present disclosure.

The controller 200 may be a stand-alone computing device similar in many respect to the computing device 400 of FIG. 4, or integrated into one or more of the various components of the robotic surgical system 10 (e.g., in the tower 116 or the console 300). The controller 200 may also be distributed to multiple components of the robotic surgical system 10 (e.g., in multiple towers 116. The controller 200 generally includes a processing unit or processor 206, a memory 208, the tower interface 204, a console interface 202, and an imaging device interface 210. The tower interface 204, the console interface 202, and the imaging device interface 210 communicate with the tower 116, the console 300, the imaging devices 414, 416, respectively, via either wireless configurations, e.g., Wi-Fi, Bluetooth, LTE, and/or wired configurations. Although depicted as a separate module, the console interface 202, the tower interface 204, and the imaging device interface 210 may be a single component in other embodiments.

The console 300 includes input handles 302 supported on control arms 304 that enable a clinician to manipulate the surgical robot 100 (e.g., move and engage the robotic arms 102, the ends 104 of the robotic arms 102, and/or the tools 108) within a workspace "W". Each of the input handles 302 may allow the clinician to manipulate (e.g., clamp, grasp, fire, open, close, rotate, thrust, slice, etc.) the tools 108 supported at the ends 104 of the robotic arms 102. The motion of each of the input handles 302 through the workspace "W" may cause the ends 104 of the robotic arms 102 and/or tools 108 to move within a surgical space "S" in any scaled correspondence to cause movement of the surgical robot 100.

The console 300 further includes a computer 308, includes a processing unit or processor and memory, which includes data, instructions and/or information related to the various components, algorithms, and/or operations of the tower 116, similar in many respects to the computing device of FIG. 4. The console 300 may operate using any suitable electronic service, database, platform, cloud, or the like. The console 300 is in communication with the input handles 302 and a display 306. Each input handle 302 may, upon engagement by the clinician, provides input signals to the computer 308 corresponding to the movement of the input handles 302. Based on the received input signals, the computer 308 may process and transmit the signals to the controller 200, which in turn transmits control signals to the tower 116, and the devices of the tower 116, to effect motion based at least in part on the signals transmitted from the computer 308. The input handles 302 may be handles, pedals, or computer accessories (e.g., a keyboard, joystick, mouse, button, touch screen, switch, trackball, and the like).

The display 306 may be configured to display two and/or three-dimensional images. Specifically, the display 306 may be configured to display a user interface including image data captured by the robotic surgical system 100. When images of the surgical space "S" (e.g., visual images, infra-red images, ultrasound images, X-ray images, thermal images, and/or any other captured real-time images) are captured by the imaging device 106, 114, disposed within or about the body of the patient "P", the image data may be transmitted to the controller 200 which, in turn, may generate three-dimensional images of the surgical space "S" from the image data. These three-dimensional images may then be transmitted for display on the display 306 of the console 300.

For a detailed discussion of an exemplary construction and operation of a robotic surgical system, reference may be made to U.S. Pat. No. 8,828,023; for a detailed description of an exemplary surgical robot 100, reference may be made to International Patent Publication WO2017/210098, filed May 26, 2017; and for a detailed discussion of the construction and operation of a robotic surgical system 10, reference may be made to International Patent Application No. PCT/US18/49319, filed Sep. 4, 2018, entitled "ROBOTIC SURGICAL SYSTEM CONTROL ARM INCLUDING DUAL ENCODERS," the entire contents of each of which are incorporated herein by reference.

With continued reference to FIGS. 1 and 2, the linkages 112 further include imaging devices 106, 114, 414 supported or disposed thereon and that are configured to capture images of the surgical environment. Specifically, the imaging devices 106, 114, 414, 416 may be disposed in spaced relation to, positioned in, or along the various components of the surgical robot 100. The imaging devices 106, 114, 414, 416 are configured to capture image data of the surgical environment or the surgical space "S" (e.g., linkages 112, surgical tables, individuals, other objects, organs, etc.) and the surgical robot 100. Once captured, the imaging devices 106, 114, 414, 416 transmit the image data to the controller 200 for analysis. The imaging devices 106, 114, 414, 416 may include sensors such as, without limitation, optical sensors, imaging device sensors (e.g., CCD and/or CMOS) and/or light detection and ranging (e.g., LiDAR and time-of-flight depth) sensors which collect sensor data. As a result of the collection of sensor data, the imaging devices 106, 114, 414, 416 or the controller 200 may incorporate known data analysis techniques such as, without limitation, stereoscopic matching, light imaging detection, optical imaging, and/or ranging lasers, light detection and ranging (e.g., LiDAR) technology, and in turn, convert the collected sensor data into real-time image data (e.g., visual images, infra-red images, and other real-time images) of the surgical environment and/or surgical space "S". In embodiments, the imaging devices 106, 114, 414, 416 may transmit raw data which is later processed by remote computing devices (e.g., the controller 200 or a remote computing device) to generate the image data.

The real-time images or later-generated image data may represent the surface depth of the objects within the surgical environment relative to the respective imaging devices 106, 114, 414, 416. In embodiments, the imaging devices 106, 114, 414, 416 illuminate objects with a laser light and, in turn, the sensors may measure the amount of time it takes for the light to hit the objects and be reflected from the objects within the surgical environment or within the surgical field. For example, using LiDAR the distance of an object in the surgical environment relative to imaging devices 106, 114, 414, 416 is measured based upon the recorded time between the transmission of the light and the detection of the reflected light and the speed of light. Based on the detection and measurement of the reflected light, imaging devices 106, 114, 414, 416 convert, generate, and transmit the sensor data as image data to the controller 200. In connection with FIGS. 5 and 6, the image data may represent the depth (e.g., distance) of the surface portions of objects relative to the imaging devices 106, 114, 414, 416 in the form of spatial points. The imaging devices 106, 114, 414, 416 transmit the image data to the controller 200 via either wireless configuration or wired configurations, as described in greater detail below.

As described later in connection with the description of FIGS. 4 and 5, the controller 200 may generate one or more depth maps or point clouds based on the captured image data to identify objects within the field of vision of the imaging devices 414, 416. Based on the generation of the depth maps or point clouds, the controller 200 may identify potential collisions of objects by calculating spatial trajectories of each object in the depth maps or point clouds. In response to identifying potential collisions, image data may be transmitted from the controller 200 to the console 300 to cause the display 306 to display an indication that a collision may occur. Displaying the indication may include changing a color of one or more objects (either moving or stationary) likely to collide with another object, outlining the objects, etc. Indication of potential collisions could also be displayed by darkening the non-colliding entities in the display and highlighting the potential colliding objects exclusively. This highlighting could also be done with changing brightness or colors. The time to collision could be indicated by showing not just the objects involved but also the swept volumes in space of the objects potentially to be in contact in the future, coloring the time dependence of the shown swept volumes with differing light intensity or color maps that make it clear what is close and what is further out in time. Spatialized audio could be used as well to either direct attention to where, on the display, the collisions may occur in the not too distant future or to direct attention to the actual location on the robot itself where the possible collision could occur. In concert with this absolute indication of a location, the user could also be using an augmented reality display which could show the actual location of the potential collision using the same techniques already mentioned but rendered in a spatially correct location.

Examples of an impending collision being displayed to the user via haptic and/or vibration feedback, either in concert with the prior visual and audio feedback methods or on its own, include:

1) An arm-to-arm collision between two surgeon-controlled (connected to the input device) robot arms, whereby:
   a. Such collision may be "displayed" by haptic feedback (increasing force felt in the direction of collision);
   b. Vibrations of the handles;
   c. Instructions on the screen showing arrows (in 3D) as to where (which direction) to move the instruments such that the arm collision is avoided;
   d. All of the above;
2) An arm to arm collision between an arm that is outside of the surgical view with an arm that is seen and controlled by the surgeon, whereby:
   a. Same as "1)" above but direction instructions limited to one arm only (the one that collides);
3) Arm to person or other object, whereby:
   a. Stopping (with appropriate haptic feedback, e.g. locking the colliding arm/handle).
   b. Decreasing a maximum torque the motor can produce as the arm nears a collision with another arm or a user.
   c. Decreasing speed limits, acceleration limits, or maximum external torques that can be produced (external torque=actuator torque–gravitational torque–dynamic torque).
   d. Changing the position control gains as an arm nears a collision such that the controller becomes "softer" in the direction that the collision may occur.
   e. Also, you could increase the scaling factor as you approach a collision. This would decrease the speed and provide more reaction time as the haptic and visual feedback is displayed.

Referring now to FIG. 4, a schematic diagram of an exemplary computing device is shown and designated generally as computing device 400. Though not explicitly shown in the corresponding figures of the present application, the computing device 400, or one or more components thereof, may represent one or more components (e.g., the controller 200 or the computer 308) of the robotic surgical system 10. The controller 400 may include one or more processors 402, memories 404, input interfaces 410, output interfaces 412, wireless interfaces 414, or any desired subset of components thereof.

The memory 404 includes non-transitory computer-readable storage media for storing data and/or software which include instructions that may be executed by the one or more processors 402. When executed, the instructions may cause the processor 402 to control operation of the controller 400 such as, without limitation, reception, analysis, and transmission of sensor signals received in response to movement and/or actuation of the one or more input handles 302. In embodiments, the memory 404 includes non-transitory computer-readable storage media for storing data and/or software which includes instructions that may be executed by the one or more processors 402. The memory 404 may include one or more solid-state storage devices such as flash memory chips. Additionally, or alternatively, the memory 404 may include one or more mass storage devices in communication with the processor 402 through a mass storage controller and a communications bus (not shown). Although the description of computer readable media described in this disclosure refers to a solid-state storage device, it will be appreciated by one of ordinary skill that computer-readable media may include any available media that can be accessed by a processor 402. More particularly, the computer readable storage media may include, without limitation, non-transitory, volatile, non-volatile, removable, non-removable media, and the like, implemented in any method of technology for storage of information such as computer readable instructions, data structures, program modules, or other suitable data access and management systems. Examples of computer-readable storage media include RAM, ROM, EPROM, EEPROM, flash memory, or other known solid state memory technology, CD-ROM, DVD, Blu-Ray, or other such optical storage, magnetic cassettes, magnetic tape, magnetic disk storage or other magnetic storage devices, or any other medium which may be used to store information and which can be accessed by the computing device 400.

In embodiments, the memory 404 stores data 406 and/or one or more applications 408. Such applications 408 may include instructions which are executed on the one or more processors 402 of the computing device 400. The applications 408 may include instructions which cause an input interface 410 and/or an output interface 412 to receive and transmit sensor signals, respectively, to and from the various components of the robotic surgical system 10. Additionally, or alternatively, the computing device 400 may transmit the signals for analysis and/or display via the output interface 412. For example, the memory 404 may include instructions which, when executed, generate a depth map or point cloud of the objects within the surgical environment based on the real-time image data received from the sensors of the robotic surgical system 100. The depth map or point cloud may be stored in the memory 208 across multiple iterations for a later cumulative analysis of the depth maps or point clouds. Additionally, the memory 404 may include instructions that, when executed by the processor 402, identify potential collisions between the objects based upon the determined spatial trajectory of the objects within the space associated with the depth maps or point clouds. For example, the output interface 412 may transmit the sensor signals to a display device such as the display 306 of the console 300, or a remote display located in the surgical environment and in communication with the computing device 400, to display an indication that a collision may occur.

The memory 404 may further transmit and/or receive data via a wireless interface 414 via one or more wireless configurations, e.g., radio frequency, optical, WiFi®, Bluetooth® (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE® 802.15.4-2003 standard for wireless personal area networks (WPANs)). Although depicted as a separate component, the wireless interface 414 may be integrated into the input interface 410 and/or the output interface 412.

Figure 5:
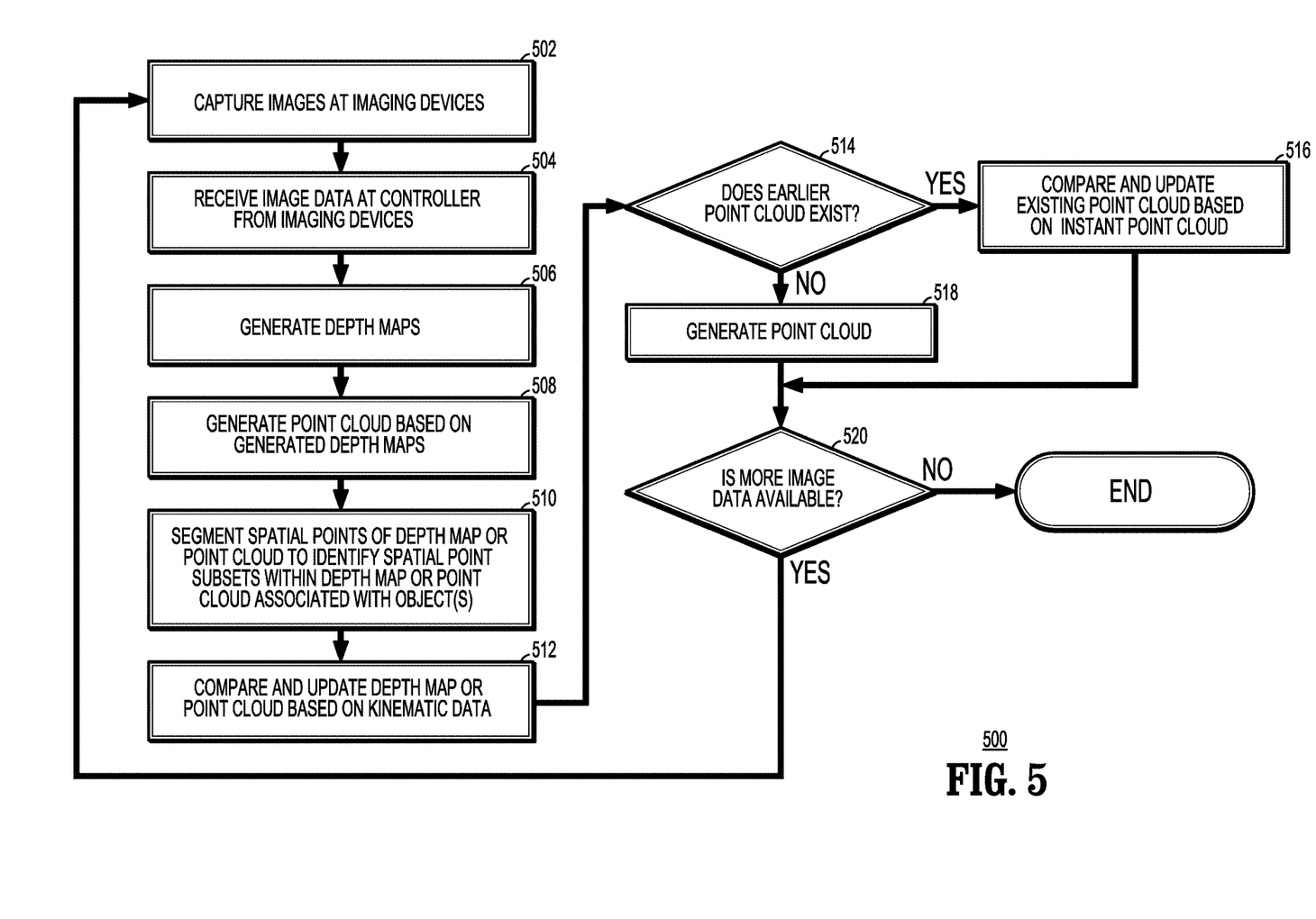
FIG. 5 is a flow diagram illustrating a method for detecting objects in the surgical environment of FIG. 1, according to an embodiment of the present disclosure.

With reference to FIG. 5, an illustrative method for generating a three-dimensional model based upon real-time images captured of robotic objects of the surgical robotic system of FIG. 1 as well as foreign objects within surgical environments, the method referred to generally as process 500.

Initially, the imaging devices 106, 114, 414, 416 capture real-time images of objects, either within the surgical environment or within a surgical space (block 502). Specifically, one or more sensors of the imaging devices 106, 114, 414, 416 capture images of objects in position relative to each of the imaging devices 106, 114, 414, 416 at one or more points in time (e.g., at varying time intervals). By way of example, the one or more imaging devices 106, 114, 414, 416 may capture real-time images at a first time point T=1 and may capture subsequent real-time image data at a second time point T=2. The real-time images captured by the imaging devices 106, 114, 414, 416 may, as described earlier, include one or more points representing a distance to a portion of the surface of the objects relative to the imaging devices 106, 114, 414, 416.

The controller 200 receives, the real-time image data transmitted from each of the imaging device 106, 114, 414, 416 (block 504). Specifically, the imaging devices 106, 114, 414, 416 transmit the captured image data (either in a raw form or processed form) to the controller 200 for analysis. Based on the received image data, the controller 200 generates one or more depth maps (block 506). The depth maps include one or more spatial points within a three-dimensional coordinate frame, each spatial point of the depth maps corresponding to a distance of a point on a surface of an object measured from the imaging devices 106, 114, 414, 416, respectively. For instance, depth maps generated at a first time point may include spatial points representing surface portions of one or more links 112a, 112b of a robotic arm 102.

The depth maps may be combined together by matching corresponding spatial points of a specific object or set of objects associated with each depth map at a particular time to produce a combined depth map, referred to commonly as a point cloud (e.g., a first three-dimensional point cloud at the first time point) (block 508). Specifically, the positional relationships between the spatial points in each of the corresponding depth maps within an X, Y, and Z coordinate grid system may be compared and matched to identify similar spatial relationships are the same (e.g., where a specific and unique combination of spatial points such as a first and second linkage 112 angled relative to one another is identified in a first depth map and a second depth map). Once identified, the sets of spatial points for each of the depth maps may be combined into a point cloud. It will be understood that, to increase the efficiency of the matching of the coordinate reference frame of each depth map, identifiable landmarks (e.g., objects with a unique shape and/or color) may be placed about the surgical environment and identified to assist during the matching of each of the reference frames of the imaging devices. Additionally, the identifiable landmarks may be identified by the controller 200 and compared to known landmarks stored in the memory 208 of the controller 200. Based on the comparison, the landmarks may be used to determine a kinematic, and by extension, physical location of one or more objects relative to one another (e.g., a linkage 112) within the surgical environment.

The plurality of spatial points within the three-dimensional point cloud are segmented to identify one or more spatial point subsets.

There are numerous methods for mapping specific collections of 3D points to the surfaces for objects and this has been and continues to be a rich area of research and development with a number of open source codes available that provide implementations of multiple approaches. The most well know is PCL, the Point Cloud Library, used with ROS (the Robot Operating System) the widely adopted and adapted code for robotics. In general the algorithms follow a sequence of processes that includes filtering, feature estimation, surface reconstruction, registration, model fitting and segmentation. Filtering typically removes bad data. Feature estimation computes specific local geometric features near some number of points such as flat planes of specific areas and magnitudes of curvature with some of form of spatial sampling often being present to limit the density of features computed. Keypoints is a variation on feature estimation that will often combine local features to discern a unique stable aspect of local geometry. Registration takes these collections of features and keypoints and searches for best statistical matches between these and aspects of the sampled point surface of objects being searched for. This can be very computationally intense so there are many approaches to accelerating this process. Model fitting takes this even further and seeks best matches of entire objects. Segmentation is usually used as an accelerator method to form isolated clusters of points and features to accelerate searching for object matches.

In one example, each spatial point within a spatial point subset that is matched with a surface portion of an object (either pre-scanned or identified across the multiple depth maps or point clouds such that the spatial point subsets may be combined together to supplement the spatial points of the identified object within the surgical environment. For example, one or more spatial point subsets may represent a robotic arm 102 of the surgical robot 100. Upon identification or matching of the robotic arm 102 in a particular depth map or point cloud, the remaining points (e.g., the points not visible to any imaging device 106, 114, 414, 416 which the controller 200 may otherwise interpret to be a void) may be updated to include the pre-scanned spatial points of known robotic arms 102 in position relative to the existing spatial points. This, in turn, enables the controller 200 to generate an image or otherwise determine possible positions or trajectories of objects within the surgical environment which would not be known.

In another example, the controller 200 may optionally generate a kinematic map based on the positions information received from one or more encoders $E_1$ disposed along or within various components of the robotic surgical system 10 (block 512). The kinematic map may include image data (e.g., a depth map or point cloud) generated that corresponds to the positions of known objects (e.g., robotic arms 102) based on the position of various encoders $E_1$ disposed about joints of the known objects (e.g., the encoders $E_1$ disposed about the joints "J" of the linkages 112 of the robotic arms 102). Where a robotic arm 102 is determined to have a particular pose (e.g., a first angle between a first and second linkage 112, and a second angle between the second linkage 112 and a third linkage 112) based on encoder signals received from encoders $E_1$ of the robotic arm 102, a kinematic map may be generated including spatial point data approximating a robotic arm 102 in such a configuration. The controller 200 may compare the generated kinematic map to the one or more spatial point subsets of the generated depth maps or point clouds identify one or more objects within the surgical environment. For instance, a kinematic map generated that represents a robotic arm 102 within the surgical environment may be compared to spatial point subsets of the depth maps or point clouds to match the spatial point subsets to the robotic arm 102.

To optimize the identification of the objects from the depth maps or point clouds, identifiable features may be placed on the objects, for example, but not limited to placing a geometric marker having a particular physical shape on an object (e.g., a robotic arm 102) and/or painting all or a portion of one or more objects with a unique color.

It will be understood that, while motion alignment of spatial points and spatial point subsets within the depth maps or point clouds are discussed as being in relation to one another (e.g., between a first and second robotic arm 102 in the surgical environment), the corresponding depth maps or point clouds may be aligned with one another, with the surgical environment, or with a particular landmark (e.g., a uniquely shaped object) within the surgical environment. Additional references may also be made to the surgical environment to improve accuracy and efficiency during the matching and comparison of the spatial points and spatial point subsets. For example, the depth maps or point clouds discussed may be aligned or oriented to the surgical environment, and by extension, the position of the objects within the surgical environment may be identified relative to the surgical environment. The depth maps and point clouds may also be oriented with the surgical environment. As a result of this orientation, the matching process may be simplified or otherwise made more efficient. Specifically, when matching spatial point subsets (e.g., a spatial point subset of a link 112a, 112b of a robotic arm 102) the controller 200 may first search a region within the depth map or point cloud where the subset of spatial points are likely to be based on earlier identification of the position of the spatial point subset relative to the surgical environment.

Once the spatial points in a depth map or point cloud are segmented (see block 510), the controller 200 may determine whether a prior depth map or point cloud was generated and stored in the memory 208 of the controller 200 (block 514). If an earlier point cloud was generated prior to segmentation of the instant depth map or point cloud ("YES" at block 516), the controller 200 compares the earlier depth maps or point clouds to the instant depth maps or point clouds. In embodiments, the controller 200 may analyze one or more spatial point subsets in a first three-dimensional point cloud, which correspond to surface portions of the objects, and match the one or more spatial points subsets of the first three-dimensional point cloud to spatial points in the second three-dimensional point cloud. In turn, the matching of the one or more spatial point subsets may assist in identifying the objects within the second three-dimensional point cloud. By way of example, the one or more spatial point subsets corresponding to a robotic arm 102 is identified from a first three-dimensional point cloud may be used to match corresponding spatial point subsets within the second three-dimensional point-cloud such to identify the robotic arm 102 at a second time period. In response, the specific object within the field of vision of the imaging devices 414, 416 (block 502) at the second time point is identified within the second three-dimensional point cloud. If it is determined at block 514 that a previous three-dimensional point cloud has not been created ("NO" at block 514), then control passes to block 518.

In one method, the objects (e.g., robotic arms 102, clinician "C" and/or "patient "P") represented by one or more spatial point subsets are extracted from the three-dimensional point cloud such to generate a three-dimensional model (block 518). The three-dimensional model represents the objects in a fixed location within the surgical environment captured by the imaging devices 414, 416 (FIG. 1) at the varying time point. The three-dimensional model may include the geometrical shape, pose and location at a fixed location (hereinafter "geometric orientation") of the objects (e.g., the robotic arms 102, clinician, patient, and other physical devices) representing the images captured by the imaging devices 414, 416 at the varying time point. For instance, in various embodiments, the first three-dimensional model is a representation of the geometric orientation of the objects extracted from the first three-dimensional point cloud at the first time point.

A determination is made as to whether a new capture real-time images demand is received from the controller 200 (block 520). For instance, to capture real-time images of the objects in the surgical environment at a subsequent time point (e.g. a second time point), and in turn, generate a second three-dimensional model. If it is determined that a new capture new real-time images command has been received ("YES" at block 520), then control passes back to block 502 to capture real-time images at the subsequent time point. If it is determined that no new captured real-time images command has been received ("NO" at block 520) then control "ENDS". As a result, by knowing where specific objects are located in the point clouds, this information may be used to accelerate the object registration process in subsequent scans.

Figure 6:
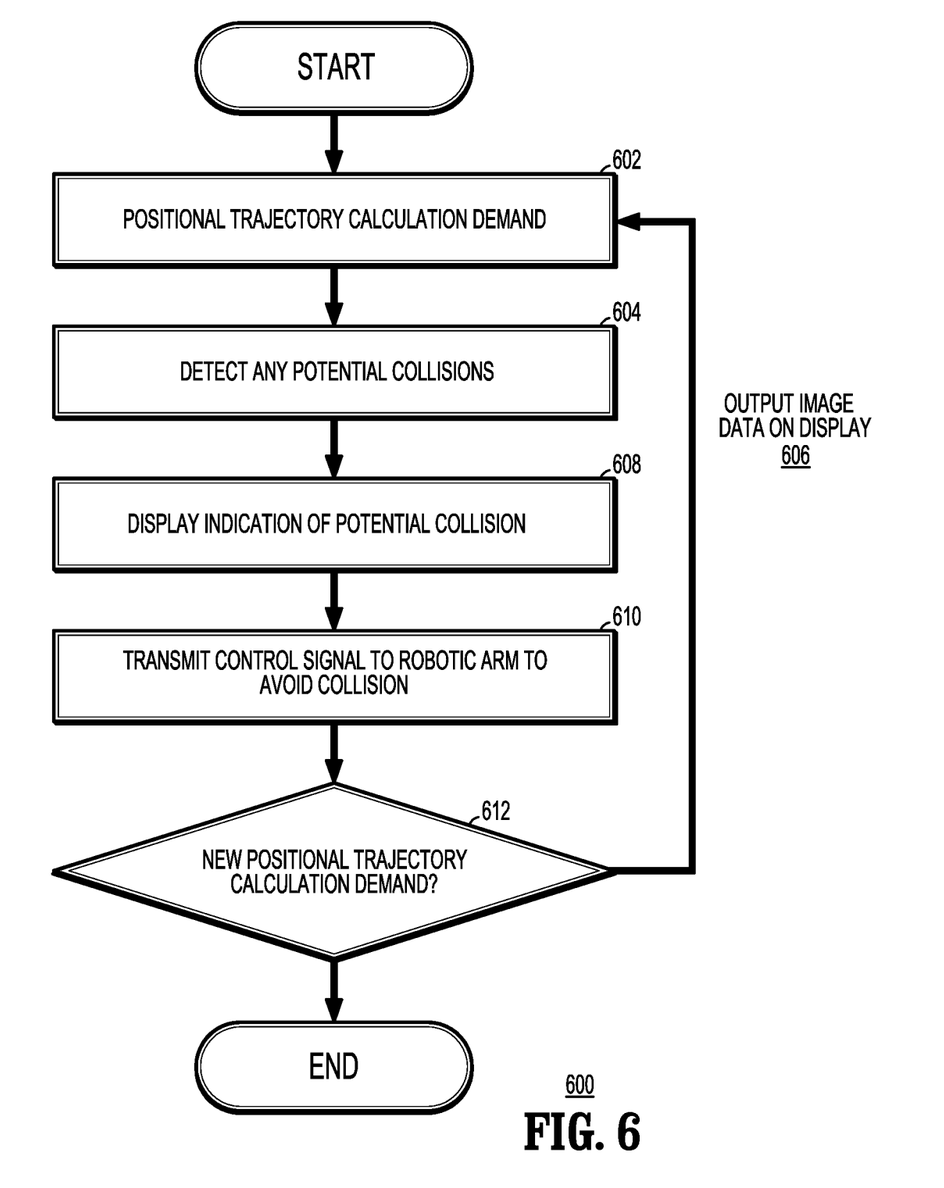
FIG. 6 is a flow diagram illustrating a method for detecting potential collisions between various components of the surgical system of FIG. 1, according to an embodiment of the present disclosure.

FIG. 6 is a flowchart showing an illustrative method for detecting potential collisions between objects in a surgical environment based upon generated three-dimensional models (see FIG. 5, process 500), the method referred to generally as process 600 with reference to the robotic surgical system 10 of FIGS. 1 and 2. As described in connection with FIG. 5, the depth maps or point clouds captured and generated based on the image data from the one or more imaging devices 106, 114, 414, 416 include spatial points which may be segmented into subsets of spatial points corresponding to the position of an object within a surgical environment. Initially, the controller 200 calculates movement trajectories of each of the objects identified during segmentation (see FIG. 5, block 510) based on each of the position and orientation of the objects across multiple depth maps or point clouds. For example, the controller 200 may a first and second robotic arms 102 may have a first and second potential trajectory which, if each of the first and second robotic arms 102 continued to move along, would lead to a collision between various components of the first and second robotic arms 102. Additionally, the controller 200 may use the positional direction of the linkages 112 in connection with the geometric orientation of each of the objects contained within the generated three-dimensional model to determine the spatial trajectory of the linkages 112 within the surgical environment.

The controller 200 detects any potential collisions between objects represented within the three-dimensional model (block 604). The controller 200 may utilize the three-dimensional model to analyze the spatial trajectory (e.g., space covered) of the objects based on the objects geometric orientation within the three-dimensional model to determine any potential collisions between objects. In various embodiments, the processor 206 may utilize swept volume assessments to analyze the spatial trajectory of each of the objects contained within the three-dimensional model. Any potential collisions between the objects may be detected by assessing whether an object's swept volume overlaps with another object's swept volume.

The controller 200 outputs image data to the display 306 of the counsel 300 (FIG. 2) (block 606). The image data transmitted to the display 306 represents three-dimensional images of potential collisions between objects within the surgical environment detected by the controller 200 based upon the three-dimensional model. The display 306 displays at least one three-dimensional image depicting the indication of a potential collision between objects within the surgical environment based on the spatial trajectory of the objects represented in the three-dimensional model (block 608).

Corrective action may be taken to avoid the indicated potential collision (block 610). Specifically, the clinician may take corrective action to avoid the potential collision displayed on the display 308. By way of example, the clinician may manipulate the robotic arms 102 of the surgical robot 100 by providing input from the input handle 302, to which in turn causes the controller 200 to transmit signals to the tower 116, and in turn effect the motion of the robotic arms 102 such to reposition the robotic arms 102 to avoid the potential collision (e.g. corrective action). Alternatively or additionally, the controller 200 may transmit signals to the tower 116 to alter the control signals to avoid the potential collision. For example, the velocity of the moving objects may increase or decrease, or the trajectory along which the objects move along may be altered or modified to avoid the potential collision. For a detailed description of an exemplary adjustment of motion of a robotic arm in a robotic surgical system based on the detection of a collision within a surgical environment, reference may be made to U.S. Provisional Patent Application No. 62/613,543, filed on Jan. 1, 2018, entitled "ROBOTIC SURGICAL SYSTEMS INCLUDING TORQUE SENSORS," now International Patent Application Serial No. PCT/2019/012015, filed on Jan. 2, 2019, the entire contents of each of which are hereby incorporated by reference.

A determination is made as to whether a new spatial trajectory calculation demand is received from the controller 200 (block 612). For instance, a new demand may be received by the controller 200 to calculate the spatial trajectory of the objects represented in a subsequent three-dimensional model (e.g., second three-dimensional model) in which the second three-dimensional model represents the geometric orientation of the objects at a second time point). If it is determined that a new spatial trajectory calculation command has been received ("YES" at block 612), then control passes back to block 602 to calculate the spatial trajectory of the objects represented in the subsequent three-dimensional model. If it is determined that no new spatial trajectory calculation command has been received ("NO" at block 520) then control "ENDS".

FIGS. 7A-7D represent image data captured by the imaging devices 106, 114, 414, 416 of FIG. 1 and analyzed by the controller 200 at varying points in time. By way of example, at a first time point (T=1) the sensors of the imaging devices 414, 416 capture real-time image data of the objects within the surgical environment "SE" (see FIG. 5, block 502). The real-time image data captured represents the depth or distance of portions of the surface of an object within the surgical environment relative to the imaging devices 414, 416. Depth maps are subsequently generated based on the image data (see block 506). The depth maps generated at T=1 comprise spatial points that correspond to surface portions of the objects within the "SE" relative to each of imaging devices 414, 416.

Figure 7A:
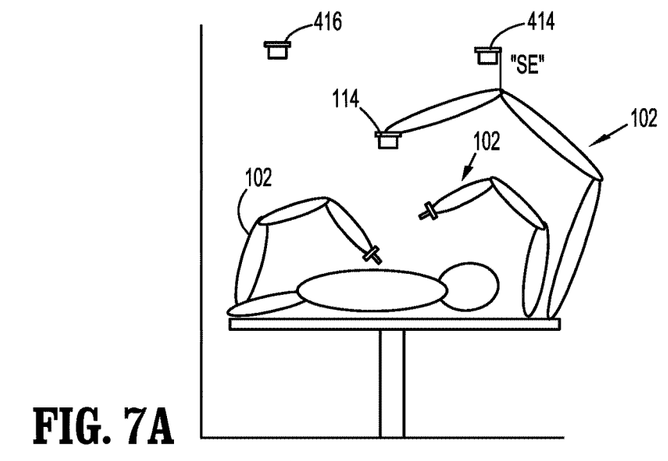
FIGS. 7A-7D illustrate exemplary image data captured by an imaging device of the robotic surgical system of FIG. 1, according to an embodiment of the present disclosure.
Figure 7B:
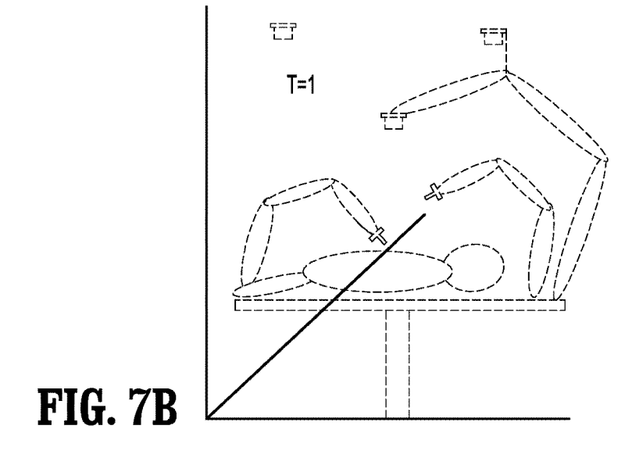
Figure 7C:
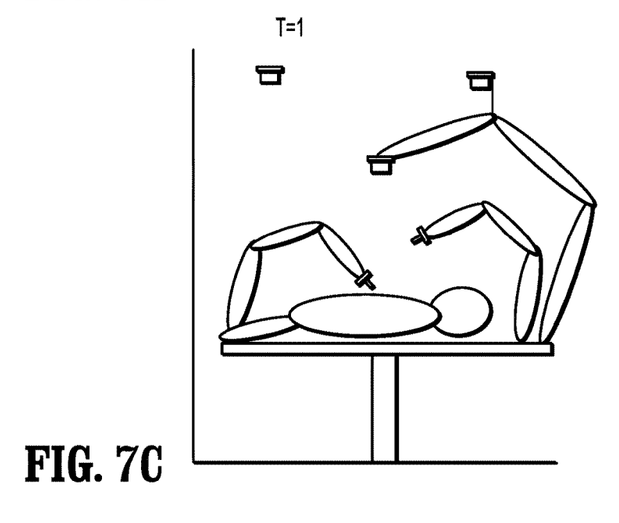

With reference to FIG. 7B, after the depth maps are segmented (see block 510) they are combined to form a point cloud (see block 518). The point cloud comprises a plurality of spatial points that represent the surface portions of the objects within the surgical environment relative to the imaging devices 414, 416 at time T=1. The plurality of spatial points of the point cloud are then segmented to identify one or more spatial point subsets to which the spatial point subsets correspond to objects within the surgical environment. Shown in FIG. 7C, once segmented, the spatial point subsets are used to generate a three-dimensional model of the associated object, in this case three robotic arms 102 in a surgical environment. The three-dimensional model represents the geometric orientation (e.g., position, pose, and shape) of each object within the surgical environment relative to one another, captured at T=1.

Figure 7D:
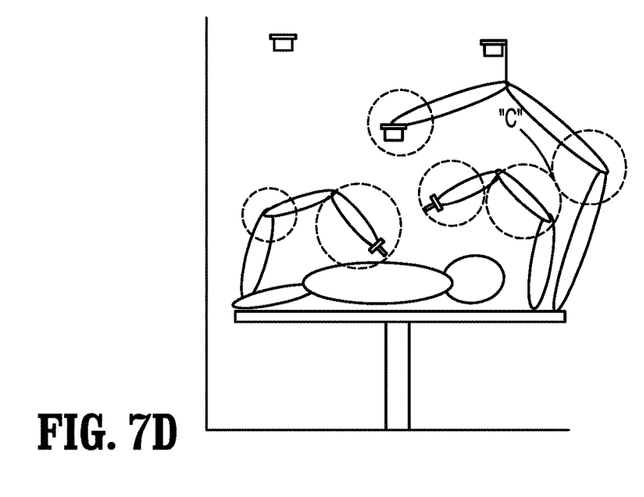

With reference to FIG. 7D, the possible trajectories of the objects are analyzed based on the geometric orientation of each object in the three-dimensional model (FIG. 7C) at T=1. Where only one three-dimensional model is available, then a known range of motion of each of the imaged objects is analyzed to determine whether the possible trajectories of the objects within the surgical environment intersect. When these potential trajectories of the objects intersect, potential collisions may be identified as likely to occur, should the objects be identified as moving along these possible trajectories. Where two or more three-dimensional models are available, the three-dimensional models, and in particular the motion of each of the objects across the three-dimensional models relative to either each other or the surgical environment, may be compared to determine where potential collisions may occur.

Based on the identification of these potential collisions, indications of potential collisions between the objects being monitored may be displayed on a display (e.g., the display 306 or a remote display (not explicitly shown) in the surgical environment, so a clinician can take action to avoid the collision, as shown in FIG. 7D. The controller 200 may also transmit modified control signals to the motors 122 of the surgical robotic system 100 to adjust movement or positioning of the objected identified as potentially subject to a collision.

In accordance with the present disclosure, identification of these potential collisions (e.g., predicting the path of the robotic arms 102 of the surgical robot 100) could be done using velocity and acceleration forward estimators, Kalman filters, or curve fitting learned from previous motions of the surgeon/surgical robot 100.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

The present disclosure provides novel systems, methods, and arrangements to assist master clinicians in teaching novice clinicians how to perform robotic surgical operations. Though detailed descriptions of one or more embodiments of the disclosed technology have been provided for illustrative purposes, various alternatives, modifications, and equivalents will be apparent to those of ordinary skill in the art without varying or departing from the spirit of the invention. For example, while the embodiments described above refer to particular features, components, or combinations thereof, such features, components, and combinations may be substituted with functionally equivalent substitutes which may or may not contain the elements as originally described.

What is claimed is:

1. A surgical robotic collision detection system, comprising:
    a robotic cart having a robotic arm;
    a plurality of imaging devices supported by the robotic cart or the robotic arm, the plurality of imaging devices configured to capture images within a field of vision of the plurality of imaging devices; and
    a controller in operable communication with the robotic arm and the plurality of imaging devices, the controller having a processor and a memory storing instructions thereon which, when executed by the processor, causes the controller to:
        receive the images from the plurality of imaging devices;
        generate a three-dimensional grid including a first plurality of spatial points from the images; and
        detect a potential collision of objects located within the field of vision based on:
            the generated three-dimensional grid;
            the geometric orientation of the objects located within the field of vision; and
            a sweep volume of movement of each of the objects located within the field of vision,
    wherein any overlap in the sweep volumes of the objects located within the field of vision provides an indication of the potential collision.

2. The system according to claim 1, wherein at least one imaging device of the plurality of imaging devices is selected from the group consisting of a stereoscopic imaging device, an optical imaging device, a ranging laser device, and an infrared (IR) imaging device.

3. The system according to claim 1, wherein at least one imaging device of the plurality of imaging devices includes a sensor configured to capture a first image at a first time point, the first image including a first object of the objects located within the field of vision in positional relation to the sensor.

4. The system according to claim 3, wherein the memory stores instructions which, when executed by the processor, causes the controller to receive the first image and generate a first depth map based on the first image.

5. The system according to claim 4, wherein the controller generates a first point cloud based on the first depth map, the first point cloud including the first plurality of spatial points contained within the grid.

6. The system according to claim 5, wherein the controller segments the first plurality of spatial points to identify a first spatial point subset of the first point cloud, each spatial point in the first spatial point subset corresponds to a surface of the first object.

7. The system according to claim 6, where the memory includes instructions that, when executed by the processor, causes the controller to:
    compare the first spatial point subset to a pre-identified configuration of a structure of the first object to identify the first object within the field of vision of the plurality of imaging devices.

8. The system according to claim 3, wherein:
    the sensor of the at least one imaging device of the plurality of imaging devices captures a second image at a second time point, and
    the memory further includes instructions that, when executed by the processor, causes the controller to:
        receive the second image; and
        generate a second depth map.

9. The system according to claim 8, where the memory further includes instructions that, when executed by the at least one processor, causes the controller to:

generate a second point cloud within the coordinate system comprising a second plurality of spatial points, and where the second point cloud is based on the second depth map.

10. The system according to claim 9, where the memory further includes instructions that, when executed by the at least one processor, causes the controller to:
segment the second plurality of spatial points to identify a second spatial point subset of the second point cloud and compare the second spatial point subset to the pre-identified configuration of a structure of the objects;
match the first spatial point subset in the first point cloud with the second spatial point subset in the second point cloud to orient the first point cloud with the second point cloud; and
identify motion of the objects within the field of vision of the plurality of imaging devices based on the orientation of the first point cloud relative to the second point cloud.

11. The system according to claim 10, wherein the memory further includes instructions that, when executed by the one or more processors, causes the controller to determine a spatial trajectory of the objects based upon the identified motion of the objects from the position of the objects in the first point cloud to the position of the objects in the second point cloud.

12. The system according to claim 1, further comprising a display device in communication with the controller,
wherein the memory further includes instructions stored thereon which, when executed by the processor, causes the controller to:
cause the display device to output an indication of a possible collision based on determining that a possible collision exists.

13. The system according to claim 12, wherein the indication includes a three-dimensional image of a position diagram.

14. The system according to claim 12, wherein the three-dimensional images of the position diagram illustrate a rendering of the possible collision at a later point in time in a case where the objects remain on the spatial trajectory.

15. The system according to claim 1, wherein the memory further includes instructions stored thereon which, when executed by the processor, causes the controller to:
transmit a control signal to the robotic cart or the robotic arm to cause the robotic arm to reposition to avoid the possible collision.

16. A method for detecting potential collisions between objects of a surgical robotic system including a robotic cart supporting a robotic arm, a plurality of imaging devices supported by the robotic cart or the robotic arm, and a controller, the controller in communication with the plurality of imaging devices and the robotic arm, the method comprising:

receiving image data of a field of vision captured by the plurality of imaging devices;
generating a three-dimensional depth map including a first plurality of spatial points based on the image data; and
detecting a potential collision between objects captured in the image data based on:
the generated three-dimensional depth map;
the geometric orientation of the objects located within the field of vision; and
a sweep volume of movement of each of the objects located within the field of vision,
wherein any overlap in the sweep volumes of the objects located within the field of vision provides an indication of the potential collision.

17. The method of claim 16, further comprising generating a first point cloud based on the three-dimensional depth map, the first point cloud comprising the plurality of spatial points.

18. The method of claim 17, further comprising segmenting the plurality of spatial points in the point cloud to identify a spatial point subset of the point cloud, each point in the spatial point subset corresponds to a surface portion of the objects.

19. The method of claim 18, wherein the identifying of the spatial point subset includes matching the spatial point subset to a predetermined configuration of the objects and, based on the matching, identifying the objects.

20. The method of claim 18, further comprising:
receiving second image data from the plurality of imaging devices at a point in time later than when the image data was captured by the plurality of imaging devices;
generating a second three-dimensional depth map including a second plurality of spatial points based on the second image data;
generating a second point cloud comprising a second plurality of spatial points based on the second three-dimensional depth map;
segmenting the second plurality of spatial points to identify the spatial point subset within the second point cloud; and
matching the spatial point subset in the first point cloud with the spatial point subset in the second point cloud.

21. The method of claim 20, further comprising:
determining a spatial trajectory of the objects based on the positional difference of the spatial point subset matched in the first point cloud and the second point cloud; and
displaying an indication of a possible collision when a possible collision exists.

22. The method according to claim 21, further comprising:
transmitting a control signal to cause the robotic arm to modify motion in a direction to avoid the possible collision.

* * * * *